United States Patent [19]

Bruno

[11] Patent Number: 4,930,631
[45] Date of Patent: Jun. 5, 1990

[54] RECEPTACLE FOR STORAGE AND DISPOSAL OF POTENTIALLY INJURIOUS IMPLEMENTS SUCH AS USED SCALPEL BLADES, HYPODERMIC NEEDLES AND THE LIKE

[76] Inventor: John Bruno, 77-83 Second Ave., Paterson, N.J. 07514

[21] Appl. No.: 406,869

[22] Filed: Sep. 12, 1989

Related U.S. Application Data

[63] Continuation of Ser. No. 344,466, Apr. 27, 1989, abandoned, which is a continuation of Ser. No. 256,186, Oct. 6, 1988, abandoned, which is a continuation-in-part of Ser. No. 833,335, Feb. 25, 1986, abandoned, which is a continuation-in-part of Ser. No. 826,288, Feb. 5, 1986, abandoned.

[51] Int. Cl.$^5$ ............................................. B65D 83/10
[52] U.S. Cl. ................................... 206/366; 220/338; 232/63
[58] Field of Search ....................... 232/15, 31, 55, 63; 220/338, 337; 206/366, 63.5, 438

[56] References Cited

U.S. PATENT DOCUMENTS

| | | | |
|---|---|---|---|
| 632,040 | 8/1899 | Brawn et al. | 232/63 |
| 915,308 | 3/1909 | Rebischung | 232/57 |
| 940,727 | 11/1909 | Quinn | 232/57 |
| 948,783 | 2/1910 | Johnson | 232/15 |
| 2,527,318 | 10/1950 | Magnus | 220/338 |
| 4,121,755 | 10/1978 | Meseke et al. | 206/306 |
| 4,315,592 | 2/1982 | Smith | 200/306 |
| 4,351,434 | 9/1982 | Elisha | 206/366 |
| 4,375,849 | 3/1983 | Hanifl | |
| 4,452,358 | 6/1984 | Simpson | |
| 4,466,538 | 8/1984 | Giannl | 206/366 |
| 4,485,918 | 12/1984 | Mayer | 206/366 |
| 4,488,643 | 12/1984 | Pepper | 206/366 |
| 4,520,926 | 6/1985 | Nelson | 206/366 |
| 4,580,688 | 4/1986 | Harris et al. | |
| 4,722,472 | 2/1988 | Bruno | |
| 4,842,138 | 6/1989 | Sandel et al. | |
| 4,869,366 | 9/1989 | Bruno | |

FOREIGN PATENT DOCUMENTS

| | | | |
|---|---|---|---|
| 13768 | 6/1904 | Norway | 232/31 |

OTHER PUBLICATIONS

Brochure for "Sharpsgard 2000" by Winfield Corp. of San Diego, CA, cira 1984.
Two (2) Brochures for "Sharpsafe" by Concord Laboratories, Inc. of Keene, NH, one circa 1984 and the other copyright 1988.
Brochure for "Sharps-A-Gator" by Devon Industries, Inc. of Chatsworth, CA, copyright 1985.
Brochure for "Eagleguard" by Amsco, American Sterilizer Co., of Erie, PA, printed 9/84.
Brochures for #8600 Series, #8950 Series and #8700 and #8720 Series devices by Sage Products, Inc. of Carey, IL, copyrighted 1981, 1982.
Advertisement for "Med-Save" Sharps Disposal System by Med-Save Systems, Inc. of Leucadia, CA, copyright 1983.
Brochure for "The Safe Deposit Box" sold by Hemox, Inc. of Highland Park, IL, copyright 1981.
Advertisement for "Hypo-Hopper" by Porex Medical of Fairburn, GA, copyright 1983.

Primary Examiner—Joseph Man-Fu Moy
Attorney, Agent, or Firm—Morgan & Finnegan

[57] ABSTRACT

A receptacle for the deposit, storage and ultimate disposal of disposable medical implements includes a containment member for storing a plurality of implements and a top assembly securable to the containment member for forming the top portion of the receptacle. The top assembly includes an opening for receiving implements, a guide member depending angularly downwardly from one edge of the opening and a back-drop/stop member depending downwardly from the opposite side of the opening, with the distal edges of the backdrop/stop member and guide member defining a slot-like gap wide enough to permit implements of predetermined size to pass in a horizontal orientation into the containment portion. In one embodiment, a closure member is pivotally mounted to the top member, preferably, integrally with the top member, by a reduced thickness web which forms a "living hinge" attachment. Also as preferably embodied, an edge of the opening and the opposite, distal, edge of the guide member have serrated edging to deter hand entry into the receptacle.

40 Claims, 8 Drawing Sheets

RECEPTACLE FOR STORAGE AND DISPOSAL OF POTENTIALLY INJURIOUS IMPLEMENTS SUCH AS USED SCALPEL BLADES, HYPODERMIC NEEDLES AND THE LIKE

CROSS-REFERENCE TO RELATED APPLICATION

This is a continuation of co-pending application Ser. No. 344,466, filed on Apr. 27, 1989, which in turn is a continuation of Ser. No. 256,186 filed 10/6/88, which in turn is a continuation-in-part of Ser. No. 833,335 filed 2/25/86, which in turn is a continuation-in-part of Ser. No. 826,288 filed 2/5/86, all now abandoned.

BACKGROUND AND OBJECTS OF THE INVENTION

The present invention relates generally to receptacles, containers and the like, and, more particularly, to receptacles for safe storage and ultimate disposal of potentially injurious or contaminated implements such as used scalpel blades, hypodermic needles and like devices which pose a risk of causing infection or even disease by exposure to such implements.

With the advent of disposable medical implements such as surgical tools, hypodermic needles, scalpel blades and other sharp implements, a need has developed for a receptacle to safely store, and safely handle for disposal, such implements after use without risk of exposing people to injury, infection or disease by improper handling, until proper disposal can be made. The tragic outbreak of the highly contagious AIDS disease has dramatically highlighted the need for safer handling, storage and disposal of such implements.

In the case of disposable hypodermic needles, it had been common practice to break or cut the needles prior to discarding the needle and syringe in order to reduce the size of the overall needle/syringe device and to eliminate the sharp point from the needle to reduce the risk of injury which might otherwise result from handling. In breaking or cutting the needles, however, a substantial danger exists of accidental puncture during the breaking or cutting operation, thus exposing the holder to possible injury and, further, to possible infection or disease as a result of such puncture. In addition, any residual medication in the needle can splatter onto the person or his clothes and there is a further danger that potentially harmful fumes can be inhaled. The blades of the cutting tool also become a breeding ground for germs, bacteria and other disease-causing micro-organisms to which the unsuspecting person cutting the needle is unnecessarily exposed.

Recently, an even greater danger has been recognized in connection with the handling and dismantling of used needles and other sharp medical implements. It is now recognized that certain diseases, most notably Hepatitis B, can be transmitted by covert percutaneous—i.e., by merely contacting the contaminated needle or implement.

As a result of the foregoing dangers, the preferred current practice is to dispose of such devices intact, without dismantling them. Often, hypodermic needles are re-capped after use with the protective sheaths used during shipment from the manufacturer, in order to prevent injury while carrying the device to a suitable disposal unit. This practice itself, however, often results in puncture wounds suffered while re-capping the needle point.

Although certain proposals have been advanced for eliminating some of the risks involved in the handling, storage and disposal of hypodermic needles and other sharp medical implements, they generally do not overcome all of the dangers. In fact, they themselves can become the source of other problems. For example, there are several specially designed containers for storing used hypodermic needles, including some made of all plastic and some made of all cardboard, as identified, for example, in my two earlier-filed co-pending patent applications (application Ser. No. 513,616, filed July 14, 1983, and application Ser. No. 746,047, filed June 17, 1985 the disclosures of which are both hereby incorporated by reference herein).

Although such specially designed devices provide adequate results under certain circumstances, they do suffer certain disadvantages as explained in my aforesaid copending applications. Of particular concern is the fact that in virtually all of these containers, either the entire syringe/needle or the syringe with the needle stub is dropped vertically into the containers, thus creating a haphazard distribution of needles in the container. Such distribution usually results in an inefficiently filled container and can be the cause of possible injury to the user who may attempt to reach into the receptacle to rearrange the implements and make room for additional implements. Furthermore, the containers will likely end up in a dangerously overfilled condition wherein personnel will attempt to "stuff" more devices than can be safely handled and thereby result in a serious risk of puncture.

As set out in my aforesaid co-pending applications, the receptacles and containers disclosed therein (also sold under the mark "D.D.BOX" by D.D.Box Inc. of Paterson, N.J. and Highland Beach, Fla.) overcome virtually all of the foregoing drawbacks. However, even with the advantages achieved by my previous containers and receptacles, some hospital administrators and other medical personnel still express a desire for a self-contained, all-plastic storage/disposal container which will provide protection against injury from or contact with discarded implements and still allow horizontal drop of implements as in my previous containers and receptacle assemblies.

One all-plastic container which attempts to provide a unitary, all-plastic, horizontal drop container is sold by Frontier Plastics under the designation "Sharpsafe". Although the "Sharpsafe" device provides generally adequate results in certain applications, it does suffer some notable drawbacks. For example, although it includes a slanted-wall chute at its opening to permit horizontal deposit of used needles, it provides no means for ensuring that the needles will remain in a horizontal orientation as they fall into the container. In addition, there is no means for preventing a person either from inserting a needle in a vertical or other non-horizontal orientation or from reaching into the container so as to risk possible puncture or injury. Moreover, a person has to rely on his or her visual depth perception when looking into the opening to determine whether the container has reached a filled or overfilled condition, and, it is not difficult to try to remove implements from the container by reaching into it especially when filled or overfilled. It also involves three separate parts that are assembled by a somewhat complicated interfitting arrangement.

Accordingly, it is an object of the present invention to provide a new and improved receptacle for storage and disposal of hypodermic needles, scalpels and other sharp or pointed implements which pose a health risk by reason of injury, puncture or even mere contact (hereinafter referred to collectively as "potentially injurious implements", or simply "disposable implements"). It is another object of the present invention to provide a new and improved receptacle for storing potentially injurious implements, which is sturdy and resistant to puncture by the implements retained therein, yet permits convenient and complete disposal of the implements together with the receptacle.

It is also an object of the invention to provide a new and improved receptacle for storage and disposal of potentially injurious implements, which is adapted to receive implements in a compact side-by-side horizontal configuration for maximum storage capacity. It is another object of the invention to provide such a receptacle which substantially prevents implements stored therein from falling out after closure of the receptacle, and which provides a permanently sealable disposable container which can be conveniently discarded in an appropriate disposal facility. In addition, it is an object of the invention to provide such a receptacle which prevents a person's hand from contacting such implements within the receptacle.

It is yet a further object of the present invention to provide a new and improved receptacle for storing potentially injurious implements, which is compact, and can be conveniently mounted to any wall or other desired structure, yet can also be decorated for producing an attractive receptacle which can be installed in doctor offices, patient rooms or other hospital areas.

It is still another object of the invention to provide a new and improved receptacle for storing potentially injurious implements, which remains open and accessible for deposit of implements, yet passively prevents hand entry into the receptacle without requiring any moving parts such as a door, lid or like closure member which must be opened and closed.

It is still a further object of the invention to provide such a receptacle which permits simply placing the potentially injurious implements at the opening of the receptacle and ensures that each implement will be deposited in a horizontal orientation into the receptacle for efficient side-by-side stacking of implements, and prevents a person from depositing such an implement in a vertical or other non-horizontal orientation. In addition, it is an object of the invention to permit such simple deposit of the implements while substantially preventing a person's hand from reaching inside the receptacle.

It is yet another object of the invention to provide such a receptacle which facilitates a person's ability to easily recognize when the receptacle has been filled to its intended capacity or has reached an overfill or dangerous overfill condition. Furthermore, it is an object of the invention to provide a small compartment which allows the receptacle to be safely overfilled with a few additional implements when, for example, there may be insufficient time to dispose of a filled receptacle and locate a fresh one.

It is yet a further object of the present invention to provide a new and improved receptacle of the foregoing type which includes mounting means adapted to provide further resistance to hand entry into the receptacle, yet still permits easy visual detection of the overfill condition.

It is also an object of the invention to provide a receptacle of the foregoing type which is adapted to permit relatively simple but secure closure of the receptacle when filled. Further, it is an object of the invention to provide such a receptacle which is adapted to permit full closure even if the receptacle has reached the overfilled or dangerously overfilled condition.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention comprises a receptacle for the deposit, storage and ultimate disposal of disposable medical implements, which includes a containment member adapted to store a plurality of implements and a top assembly securable to the containment member for forming the top portion of the receptacle. The top assembly includes an opening for receiving implements to be stored in the receptacle, a guide member depending angularly downwardly from adjacent one edge of the opening and a back-drop/stop member depending downwardly from the top member along a portion of the opposite side of the opening from the guide member, with the distal edges of the backdrop/stop member and guide member defining a slot-like gap wide enough to permit implements of predetermined size to pass in a horizontal orientation into the containment portion.

As preferably embodied, a closure member is provided for sealing the opening in the top member after the receptacle is filled. In one embodiment, the closure member can be snap-fit over the opening, preferably along a recessed shoulder formed along at least portions of the rim of the opening so that it is essentially flush with the top surface of the top member to resist prying open. In another embodiment, the closure member is pivotally mounted to the top member. The pivotal mounting may be accomplished either by a pin and recess arrangement or by a forming the closure member integrally with the top member, attached by a reduced thickness web which forms a "living hinge" attachment.

Also as preferably embodied, an edge of the top member opening and the opposite, distal, edge of the guide member have oppositely projecting jagged or serrated edging to deter hand entry into the receptacle. Further advantageously, either or both of the top and containment members include a slotted flange to allow mounting to a wall bracket which, preferably, can be locked.

According to a further preferred aspect of the invention, the mounting flange is located along the edge closest to the joinder of the sloping guide member. By such location, the guide member not only blocks visual observation of the interior of the receptacle, but also increases the difficulty for a person to attempt hand entry into the receptacle, yet it still permits readily visible recognition of an overfill condition.

As further preferably embodied, the back-drop/stop is adapted to be relatively flexible so that it will yield when subjected to a force, such as needles being urged against it when the closure member is closed against any needles that may be located at the mouth of the receptacle opening. Such flexibility may be provided either by tapering the back-drop/stop or by reducing the thickness of the back-drop/stop along its line of joinder with the top member, as by forming a weakened line of attachment.

It will be appreciated by those skilled in the art that the foregoing brief description and the following detailed description are exemplary and explanatory of the invention, but are not intended to be restrictive thereof. Thus, the accompanying drawings, referred to herein and constituting a part hereof, illustrate preferred embodiments of the invention and, together with the detailed description, serve to explain the principles of the invention.

DETAILED DESCRIPTION OF PREFERRED EMBODIMENTS

Figure 1:
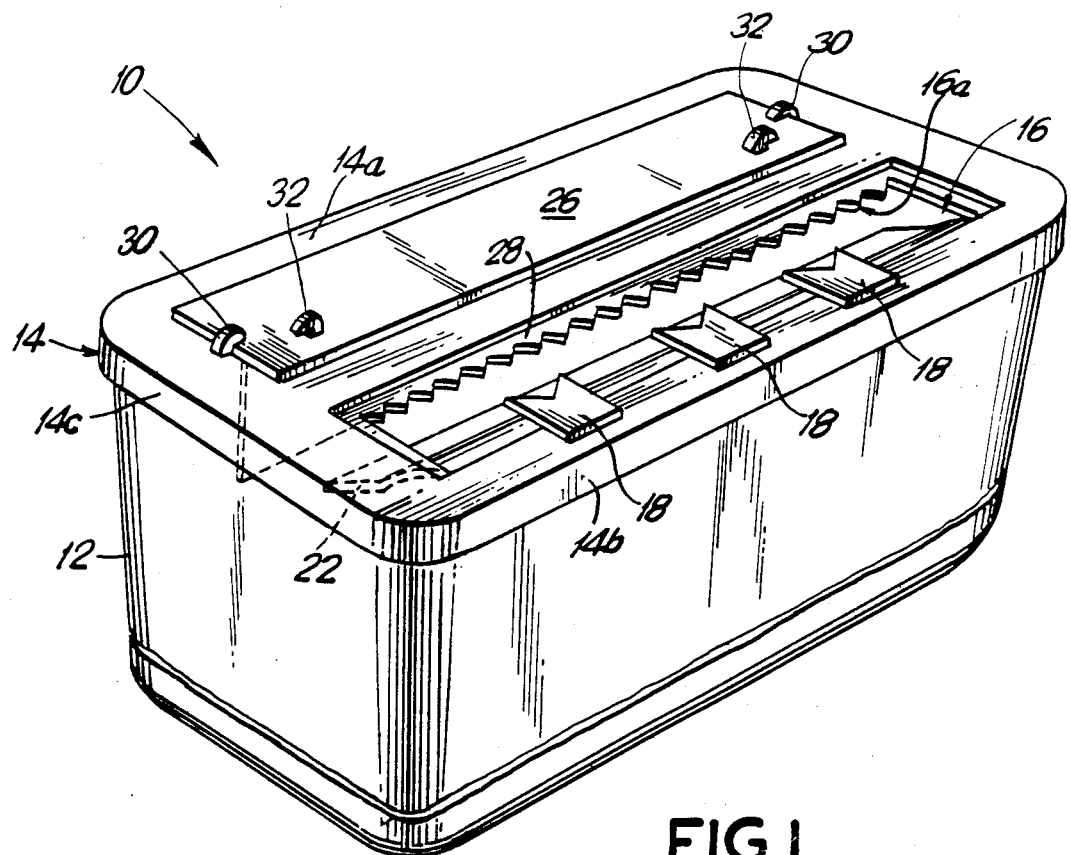
FIG. 1 is an isometric view of one preferred embodiment of a receptacle according to the present invention.

Turning now to the accompanying drawings wherein like reference characters refer to like parts throughout the various views and in the various embodiments, there is shown in FIGS. 1-6, one preferred embodiment of the receptacle (indicated generally at 10) for receiving and storing potentially injurious implements according to the present invention.

As here embodied, receptacle 10 comprises a container-like housing which, for convenience of fabrication, includes a containment member (12) which provides sufficient volume to enable storage of a desired number of implements, and a top member (14) which provides means for safely depositing the implements into the receptacle in a horizontal orientation for efficient storage in the chamber portion while preventing a person from reaching his hand into the receptacle in accordance with the present invention. It will be understood that containment member 12 is proportioned to accommodate any size implement desired and any number thereof. Since the top and containment members are advantageously made separately for ease of fabrication (e.g., by simple two-part injection molding techniques) they may preferably include any known secure means for locking them together, such as interlocking sear members (13a) formed on top member 14 and lip members (indicated at 13b in FIG. 11) formed along the top rim of containment member 12.

It will also be understood that the material and wall thickness of containment member 12 should be selected to ensure that none of the implements stored therein can damage it or cause poke-through. For example, for most commonly used thermoplastic materials, the wall thickness should be at least about 40 thousanths of an inch (0.040") thick and more preferably at least about 50 thousanths of an inch (0.050") thick. As preferably embodied, top member 14 should likewise be made of a material and wall thickness which are sufficiently strong and resilient to withstand the repeated deposit of implements and provide a secure closure of the receptacle. Advantageously, top member 14 includes a top wall 14a with two oppositely disposed downwardly extending side walls 14b and two oppositely disposed downwardly extending end walls 14c to lockably engage the containment member. It will be understood that the sear and lip engagements between top member 14 and the upper rim of containment member 12 provide a secure interlock between the two members while the continuous depending side and end walls, 14b and 14c, provide a protective skirt around the top of containment member 12 to prevent access into the receptacle along the line of joinder between these two members.

Top member 14 is adapted to recieve disposable implements as large as 60 cc syringes yet prevent a person from reaching his or her hand into the receptacle to touch the implements stored therein. To this end, the top member 14 includes a generally rectangular opening 16 which is at least long and wide enough to receive the largest implement (including the flange on a syringe) desired to be stored in the receptacle. Thus, for example, for a 60 cc needle and syringe opening 16 may be about 8-12 inches long and about 1¾-2½ inches wide.

Advantageously, guard tabs 18 may be formed along one or both side edges of opening 16 to allow passage of the implement while preventing access into the receptacle by a person's hand. Advantageously, there are at least two guard tabs and they are provided with sharply pointed distal edges, as indicated at 18a in FIG. 2. It will be understood that, to ensure a person's hand will not fit through opening 16 and into the receptacle, the spacing between adjacent guard tabs 18 should be about 3½-4 inches or less, and, the spacing between the distal points 18a and the opposite edge of opening 16 should be no greater than about 1⅛ inches which will still allow 60 cc syringes to pass through the opening. Depending on the size of implements to be deposited in the receptacle, the distance between the distal edge of guide panel 22 and the top wall 14a may be as much as about 1½" to accept 60 cc syringes and the spacing between the distal edge of panel 22 and back-drop panel 24 may likewise be about 1½".

Figure 2:
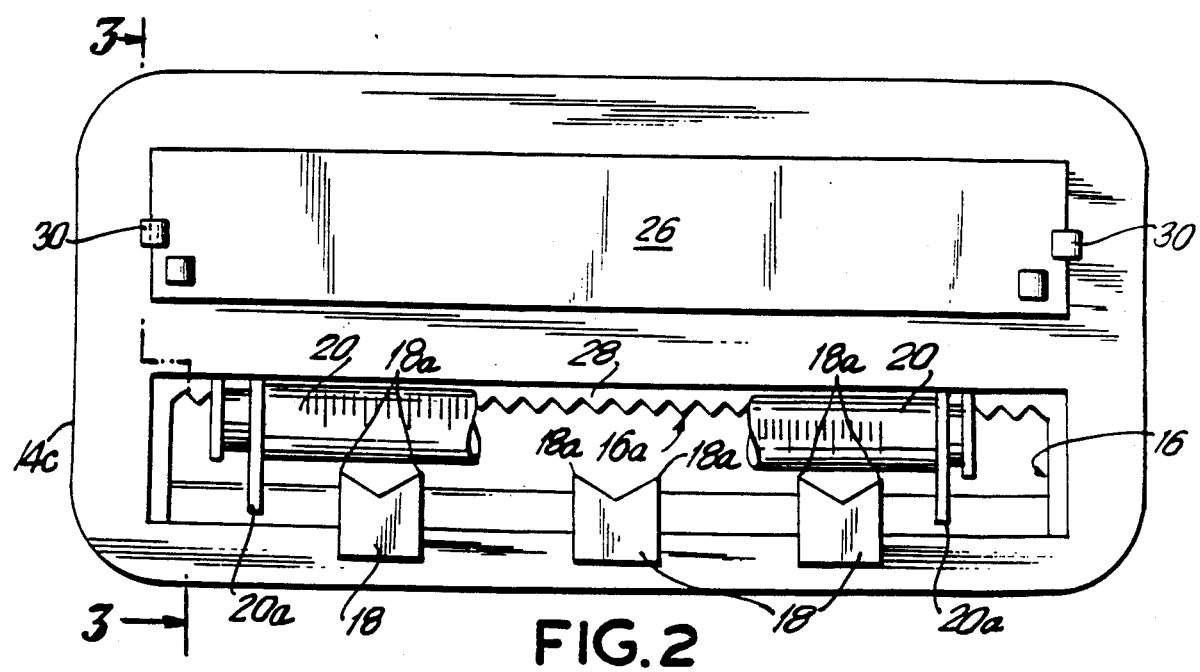
FIG. 2 is a top view of the receptacle embodiment shown in FIG. 1.

Advantageously, the edge of opening 16 opposite distal points 18a has a serrated or sharp saw-tooth edge, as indicated at 16a in FIG. 2, to further deter a person from trying to reach his or her hand through opening 16. Thus, as shown in FIG. 2, introduction of a large needle/syringe (indicated at 20) is carried out simply by laying it horizontally over opening 16, with the syringe flange (20a) located in a space between one of the guard tabs 18 and the end edge of opening 16, so it will drop through opening 16 simply by the action of gravity.

Figure 3:
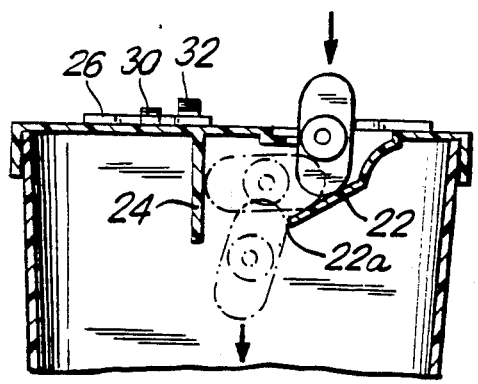
FIG. 3 is a sectional view taken along lines 3—3 of FIG. 2.
Figure 5:
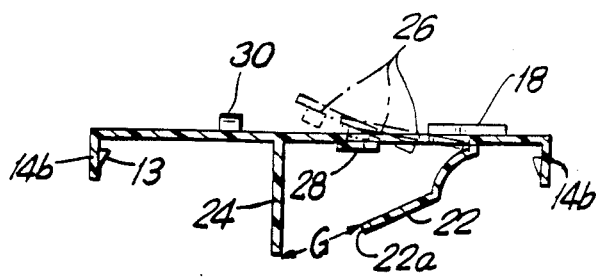
FIG. 5 is another sectional view similar to FIG. 4 showing the closure sequence for the embodiment of receptacle illustrated in FIG. 1.
Figure 4:
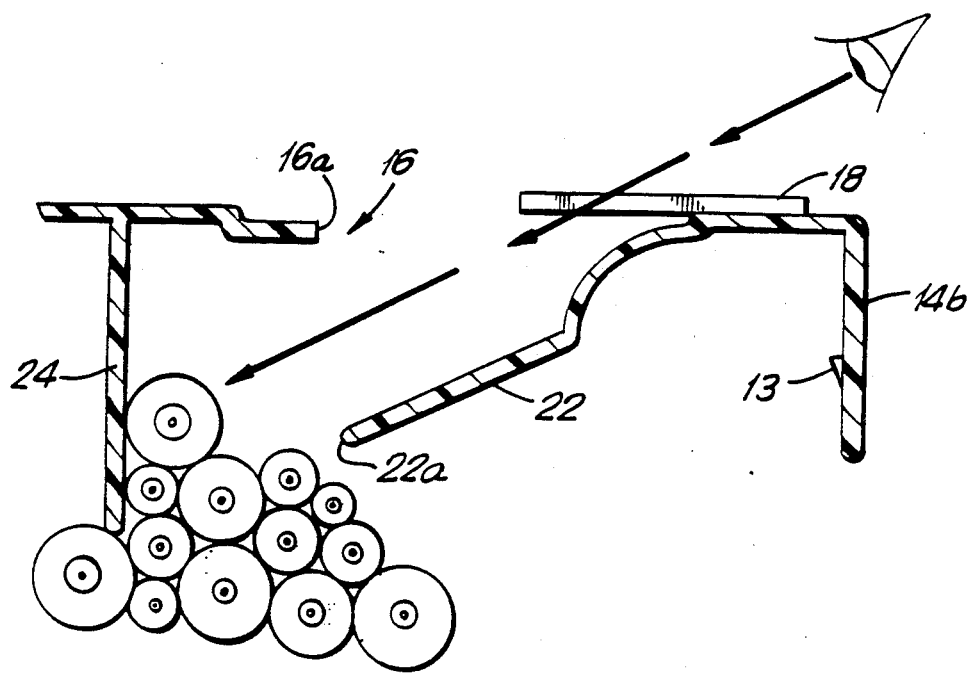
FIG. 4 is an enlarged sectional view similar to FIG. 3 illustrating how a person can easily inspect the receptacle to determine whether the receptacle has reached the filled or overfilled condition.

Turning now to FIGS. 3–5 there are shown additional features according to the invention. Top member 14 advantageously includes panel-like guide member 22 extending angularly inwardly from an inward edge (here, the front inward edge) of opening 16 to guide the implements into the containment member once they are past opening 16, as will be described more fully hereinafter. Advantageously, guide panel 22 extends from the same edge as guard tabs 18 to facilitate fabrication by two-part injection molding techniques. It will be understood by those skilled in the art that guide panel 22 may be formed with openings corresponding in shape to guard tabs 18 in order to form tabs 18 by such molding techniques.)

As further preferably embodied, the inwardly projecting distal edge (indicated at 22a) of guide panel 22 is serrated or otherwise formed with a sharp or jagged saw-tooth edge similar to edge 16a, to further deter a person from reaching into the receptacle. Jagged edge 22a may be used in addition to or instead of guard tabs 18. For ease of molding, it may be preferable to form only the oppositely projecting jagged edges 16a and 22a which, in combination with the somewhat tortuous entry path provided by members 22 and 24, should be sufficient to deter hand entry into the receptacle.

Also advantageously and as preferably embodied, top member 14 includes back-drop/stop member, here in the form of panel-like wall 24 which extends perpendicularly from top wall 14a. Back drop/stop 24 not only cooperates with guide panel 22 to ensure that implements drop into the receptacle in a horizontal orientation and that hand entry is deterred, but it also acts as a visual back drop to facilitate inspection of the interior of the receptacle to determine whether the receptacle is filled or over-filled.

Figure 6:
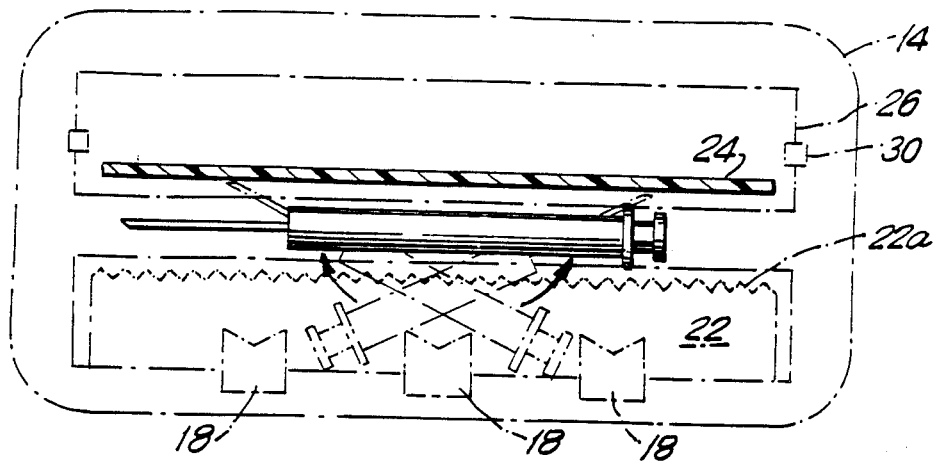
FIG. 6 is a top view, partially in phantom, of the receptacle embodiment shown in FIG. 1, showing how the invention prevents deposit of implements in a non-horizontal orientation.

In operation, once an implement is dropped through opening 16, it travels (by sliding or rolling) along guide member 22 under the influence of gravity until it reaches back-drop/stop 24. Member 24 momentarily slows/stops travel of the implement to ensure that it is aligned in a horizontal orientation and parallel to the walls of containment member 12, before it free-falls, through the slot-like gap (G) between the distal edges of members 22 and 24, into containment member 12, as illustrated in FIG. 3. In this way, the implements will land and become horizontally stacked (generally parallel to the receptacle walls) in side-by-side relation for the most-efficient packing of implements. Moreover, as illustrated by FIG. 6, it will be readily apparent that even if a person tries to introduce implements in a configuration other than a generally horizontal orientation, the implements will necessarily become re-oriented to a horizontal orientation by the co-action of their impact against guide member 22 and back-drop/stop 24. Thus, if a person tries to insert a needle/syringe at a 45° angle relative to the receptacle walls (as indicated in phantom in FIG. 6), the guide panel 22 and back-drop panel 24 will force the implement to assume the horizontal/parallel orientation described above (as indicated by the darkened implement shown in FIG. 6).

FIG. 4 illustrates how back-drop panel 24 also aids a person's visual inspection of the level of fill in the receptacle. As the receptacle is filling, the level of implements rises. However, without back-drop panel 24, a person would have to rely on his or her visual depth perception while looking through a slot or opening to determine whether a receptacle is filled, and it may be very difficult to determine whether it has reached an overfilled or a dangerously overfilled condition where no further implements should be deposited. With the back-drop panel, one can easily determine by a quick glance whether the receptacle is filled because an implement will be immediately visible against back-drop panel 24, as can be seen from the illustration in FIG. 4. Of course, it will be understood that the receptacle can be gently tapped to ensure that the implements are settled in the receptacle so that it will fill to capacity.

The combination of back-drop/stop 24 and guide member 22 are further advantagious in providing a small chamber above the containment member to recieve a few additional implements, thereby allowing the receptacle to be overfilled without reaching a dangerously overfilled condition, (e.g., with sharp points immediately at, or protruding from, opening 16), and, it permits an immediately visible indication that the receptacle has reached an overfill condition. Thus, guide panel 22 acts as a guide for deposit of implements, a barrier against insertion of a person's hand, and an overfill tray do help support a few additional implements without resulting in a dangerous overfill condition.

Referring to FIG. 5, there is illustrated one embodiment of closure means according to the invention for securely closing the receptacle after it has been filled with implements and ready for disposal. As here embodied, the closure means includes an essentially flat closure panel 26 which is proportioned to fit fully over opening 16. To secure closure panel 26 in place, a recessed shoulder or shelf is formed (indicated generally at 28) at least along the side of opening 16 opposite guard tabs 18, with a comparable shoulder or shelf preferably formed along the side on which guard tabs 18 are formed. To this end and advantageously, guide panel 22 includes a curved portion adjacent its point of connection to top wall 14a so as to create a shelf or shoulder to receive one edge of closure panel 26. The curvature also facilitates sliding of the panel during the closure step.

In operation the closure panel 26 can be slidably stored adjacent opening 16 under lips formed in oppositely disposed storage lugs 30 formed on the top of top wall 14a, as illustrated in FIGS. 2 and 3. When the receptacle is filled and is ready for closure, closure panel 26 is removed from lugs 30 and moved towards opening 16 with one side edge slid under guide tabs 18 until seated in abutting relation with the opposite edge of opening 16, as indicated in full lines in FIG. 5. At the same time, the opposite side edge of closure panel 26 becomes seated on shoulder 28. Advantageously, in order to ensure secure closure of the receptacle, one or more sear-like locking tabs (indicated at 32 in FIG. 3) may be formed on bottom surface of closure panel to snap into place under the opposite end edges of opening 16.

Alternatively and advantageously, the closure panel may be pivotally mounted to top member 14 to further facilitate closure of the receptacle.

Figure 7:
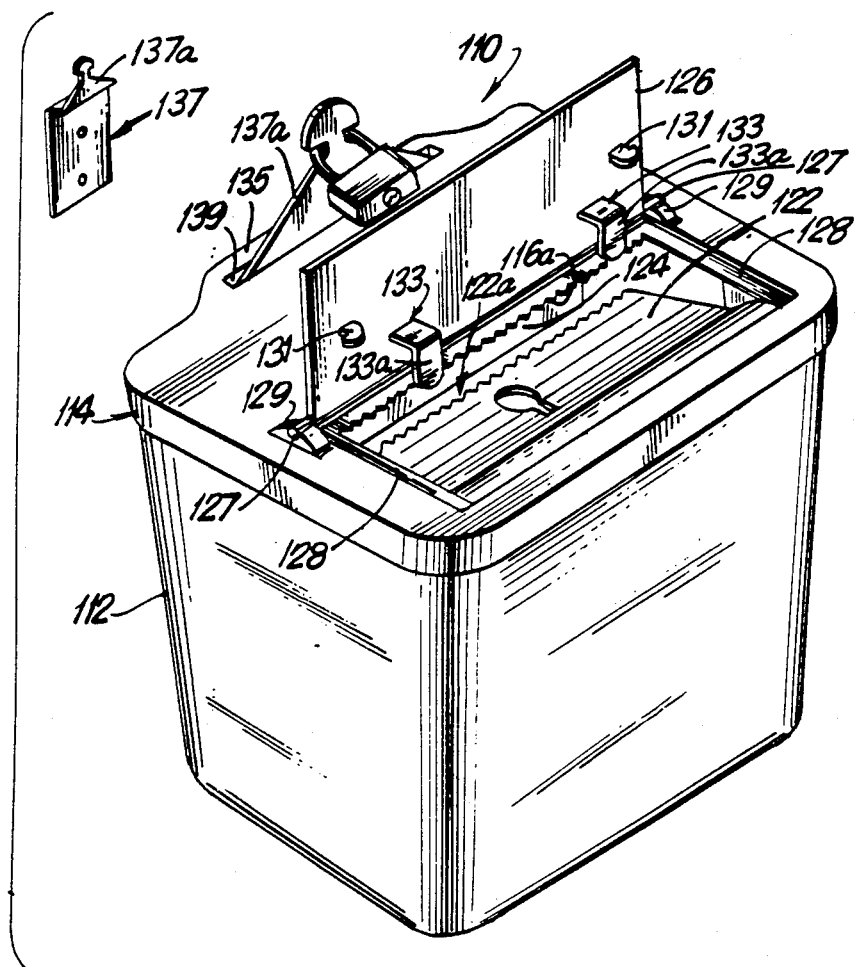
FIG. 7 is an isometric view of another preferred embodiment of a receptacle according to the present invention.

In one embodiment, shown in FIG. 7, the closure panel (indicated at 126) may be formed with a pair of rod-like projections (each designated 127) to act as the hinge pin for enabling pivotal connection of closure panel 126 to top member 114. (In essentially all other respects, top member 114 is the same as top member 14 described above with reference to FIGS. 1-6. Thus, like parts will be indicated by similar numbers, e.g., top members 14, 114 and 214, back-drop/stop 24, 124 and 224, etc.) Top member 114 includes means for recieving rod-like members 127 in order to permit pivotal movement (appoximately 180°) of closure panel 126.

As here embodied, the recieving means are in the form of lugs 129 in which are formed recesses (not numbered) which are proportioned to recieve (in a snapping action) and retain rod-like members 127 in such a way as to permit pivotal movement of the closure panel.

To ensure secure closure of the receptacle after it is filled with implements, the bottom of closure panel 126 includes a pair of sear-like locking tabs (each indicated at 131) proportioned and positioned to cam over their corresponding side edges of opening 116, thereby to securely lock cover panel 126 to the top member 114. In order to prevent the cover panel from being easily pryed off at hinges 127/129, one or more L-shaped locking tabs 133 are preferably formed at the back edge of closure panel 126. The parallel legs of (133a) tabs 133 will project under the bottom surface of top member 114 when panel 126 is closed to ensure that the hinged edges cannot be pried open.

Also illustrated in FIG. 7 is flange 135 which may be formed along the back edge of top member 114 to facilitate lockable mounting to a wall bracket (indicated generally at 137). To this end, flange 135 is formed with a slot 139 for insertion of bracket tongue 137a which is advantageously adapted to recieve a lock for securing the receptacle in place. Bracket tongue 137a may be formed with a notched segment as illustrated in FIG. 7 to recieve a lock shackle, or it may simply include one or more apertures to recieve the shackle. It will also be understood that the containment member can also be formed with a slotted flange through which the bracket can project to support both members of the receptacle and to lock them together.

Figure 8:
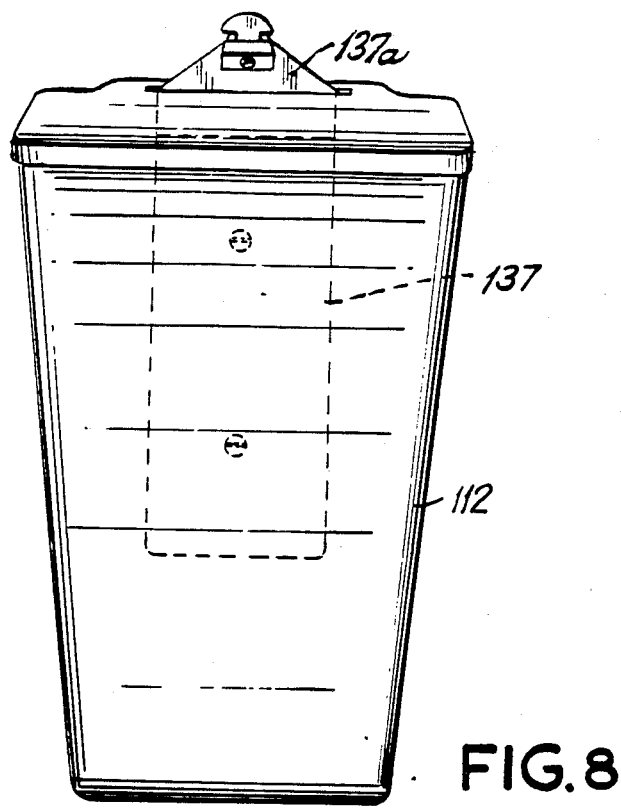
FIGS. 8 and 9 are front and side views, respectively, of a receptacle installed by wall mounting according to the present invention.
Figure 9:
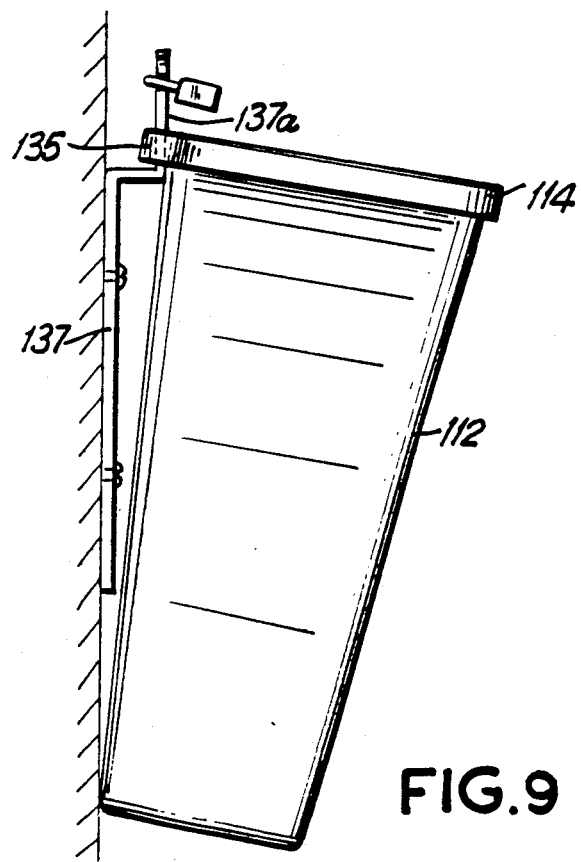

FIGS. 8 and 9 illustrate how bracket 137 can be mounted to a wall and the receptacle secured to the bracket. It will be understood that the bracket can be mounted by screws or any other convenient fasteners since they will be covered by the receptacle and thereby rendered inaccessible by unauthorized personnel. It will also be understood that the containment member can also be formed with a slotted flange through which the bracket can project to support both members of the receptacle and to lock them together.

Figure 10:
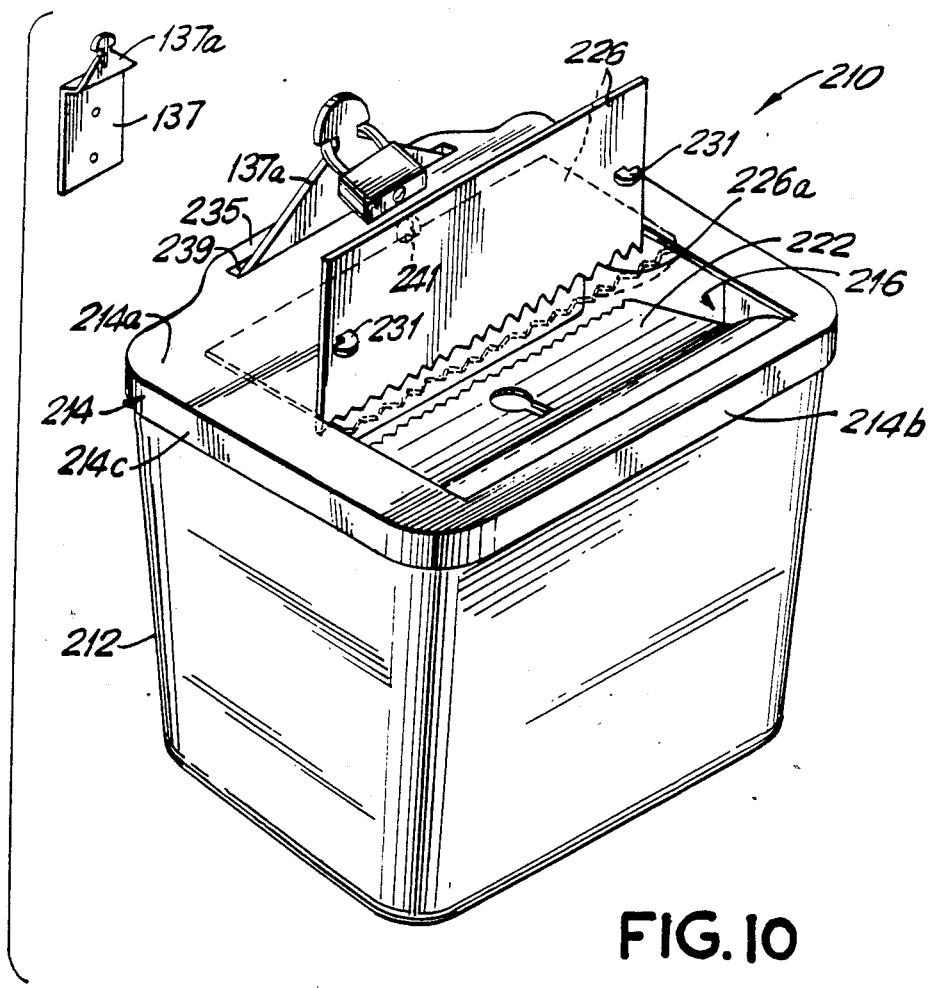
FIG. 10 is an isometric view of still another preferred embodiment of receptacle according to the present invention.
Figure 11:
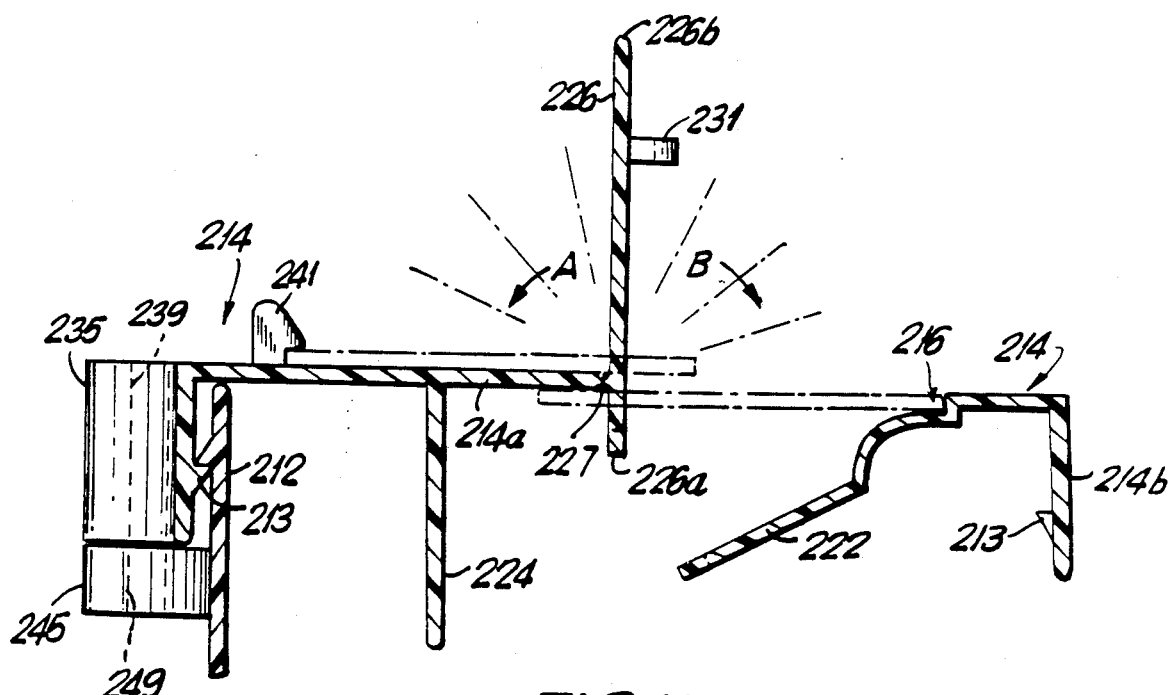
FIG. 11 is a sectional view of the top member of the embodiment illustrated in FIG. 10.

Referring now to FIGS. 10 and 11, there is shown still another preferred embodiment of receptacle according to the present invention. According to this embodiment, the closure panel (here indicated at 226) is advantageously formed integrally with top member 214, preferably by means of a "living hinge" arrangement. As here embodied, panel 226 is integrally attached along the back edge of opening 216 by reduced thickness web 227 which serves to provide a "living hinge" connection of panel 226 to the top wall 214a of top member 214. It will be understood by those skilled in the art that the foregoing integral formation and "living hinge" arrangement still permit top member 214 to be fabricated by simple two-part injection molding techniques, and, enable the overall receptacle to be made from only two separate parts which can snap-fit together for relatively easy and inexpensive fabrication and assembly.

Advantageously, top member 214 can be molded essentially in the configuration illustrated in full lines in FIG. 11 by two-part injection molding techniques. It thus includes top wall 214a with depending oppositely disposed side walls 214b and oppositely disposed end walls 214c. It further includes angularly downwardly extending guide panel 222 (with a saw-tooth or otherwise jagged distal edge substantially as described above with references to FIGS. 1-6) and downwardly projecting back-drop/stop 224. Closure panel 226 is attached by thinned web/"living hinge" 227 and may extend generally perpendicular to top wall 214a and parallel to back drop 224. In addition, the inward edge (indicated at 226a) of closure panel 226 is advantageously formed with a saw-tooth or other jagged edging. It will thus be appreciated that when closure panel 226 is folded back in the direction of arrow A and held open by latch tab 241, jagged edge 226a of the closure panel projects into opening 216 to deter a person from reaching into the receptacle, in substantially the same way as the jagged edge lip 16a disclosed above with reference to FIGS. 1-6.

After the receptacle is filled closure panel 226 can thence be rotated in the direction of arrow B until lock tabs 231 engage the opposite end edges of opening 216 to close the opening. To facilitate engagement and release of panel 226 from latch tab 241, the outward edge (indicated at 226b) may be rounded. Once the closure panel is so secured over opening 216, the implements are safely stored therein, and the receptacle can even be turned upside-down without risk that implements will fall out. Thereafter, the filled receptacle can be taken to an incinerator or other appropriate disposal unit for ultimate disposal, both the receptacle and its contents.

Advantageously, in order to facilitate molding by two-part injection molding techniques, the distal edge of the guide member may terminate at about a point directly below the opposite edge of the implement-receiving opening (i.e., the edge formed with jagged edging 16a, 116a or 216a). The back-drop/stop member may thus be recessed away from such opening edge to provide sufficient spacing to create the gap (G) between the distal edges of the guide member and the back-drop/stop member. This arrangement still provides a sufficiently tortuous path to deter hand insertion into the receptacle.

It will also be understood that a tear-drop shaped aperture may be formed in the guide members (as indicated in FIG. 7) to facilitate removal, if desired, of the needle portion from a syringe. The needle hub is simply wedged into the narrow portion of the aperture. The syringe portion is twisted until the needle is released, whereupon the needle will fall into the containment member. The area around the tear-drop aperture may be thickened to withstand repeated removal operations.

FIG. 11 also illustrates the formation of dual mounting flanges on both a top member and a containment member. As here embodied, top member 214 includes flange 235 with slot 239 formed therein to permit passage of bracket tongue 137a therethrough. Containment member 212 includes flange 245 with a similar slot 249 formed therein to likewise permit passage of bracket tongue 137a. In this way, both the top and containment members can be locked together (by use of a lock shackle passing through tongue 137a), while the weight of the receptacle will be sustained by the containment member rather than by the top member alone.

Figure 12:
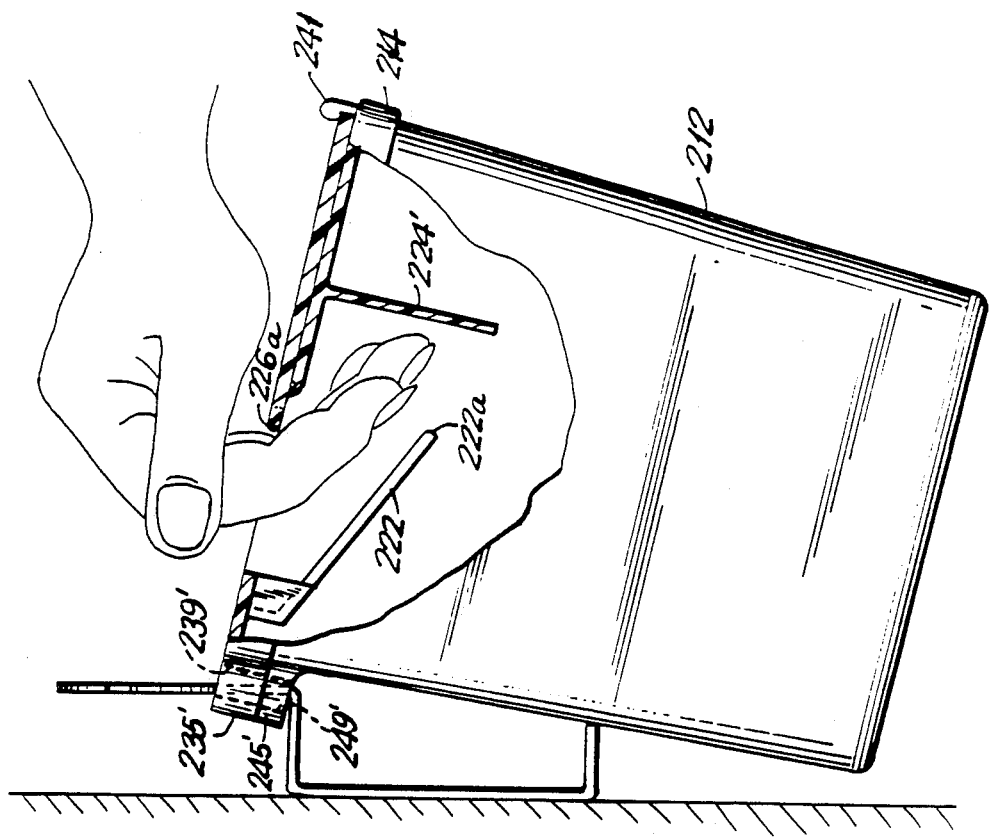
FIGS. 12 and 13 are side views, with partial cutaway, of a receptacle incorporating a preferred mounting arrangement according to the present invention.
Figure 13:
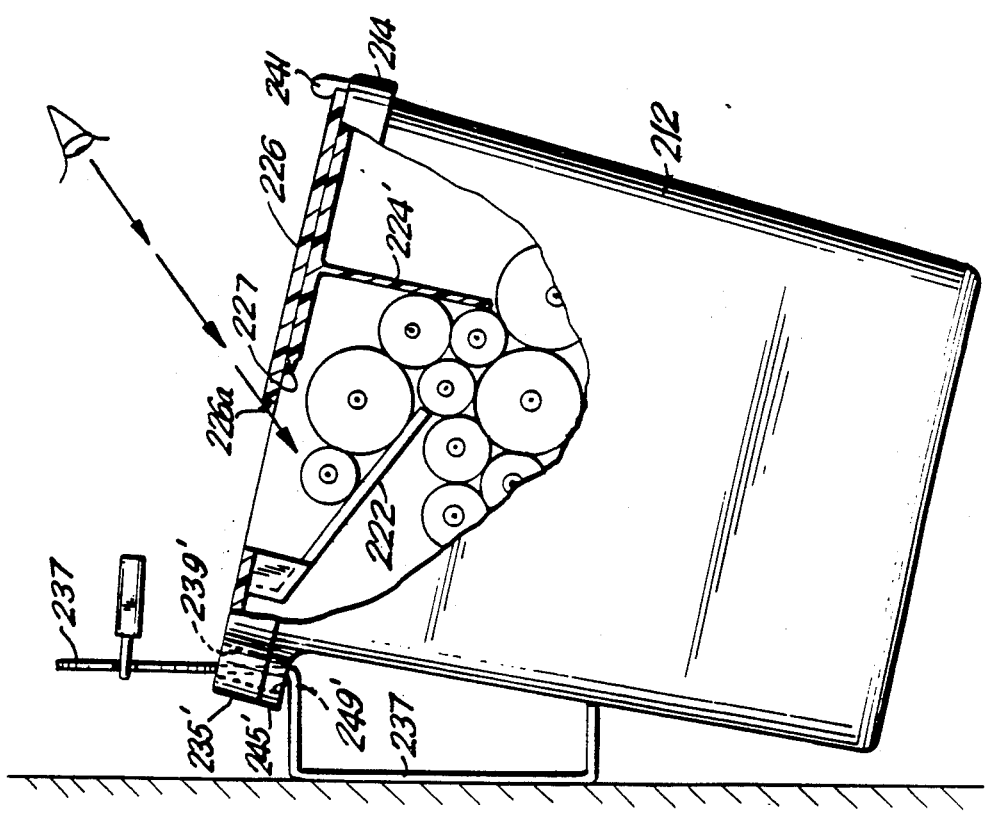

Turning to FIGS. 12 and 13, there is shown a preferred arrangement of mounting flange and bracket for mounting the receptacle to a wall. As here embodied, the slotted mounting flange (here formed both on top member 214 and on containment member 212 and indicated at 235 and 245, respectively) is advantageously formed along the receptacle edge closest to the line of attachment of guide member 222 to the top wall. The guide member thus projects away from the wall and towards a person who would be inserting used implements into the receptacle. Also advantageously, the slots 239' and 249' in the flange members are proportioned to allow the top of the receptacle to tilt slightly forward, away from the wall. Since the mounting tongue, 137a or 237a (in FIG. 13), of the wall mounting bracket, 137 or 237, will generally be spaced from the wall in order to accommodate the mounting flange, the mounting bracket will facilitate such tilting, whether or not the containment portion is tapered.

It will be understood that mounting the receptacle with the guide member projecting towards the user, the tortuous nature of the path for hand entry is even further enhanced, as indicated in FIG. 13. Moreover, since the guide member substantially blocks visual access to the contents within the containment member (except at the overfill condition), a person is, in any event, less likely to attempt hand entry into opening 216 because it means reaching into a blind opening with contaminated implements that are concealed from sight. In addition, the person's finger tips would be upside-down thereby making it difficult, if not impossible, to grasp such implements to try to withdraw them. Despite this, one can still easily observe an overfill condition because the disposable instruments will be directly visible against the guide panel 222, as indicated in FIG. 12.

Figure 14:
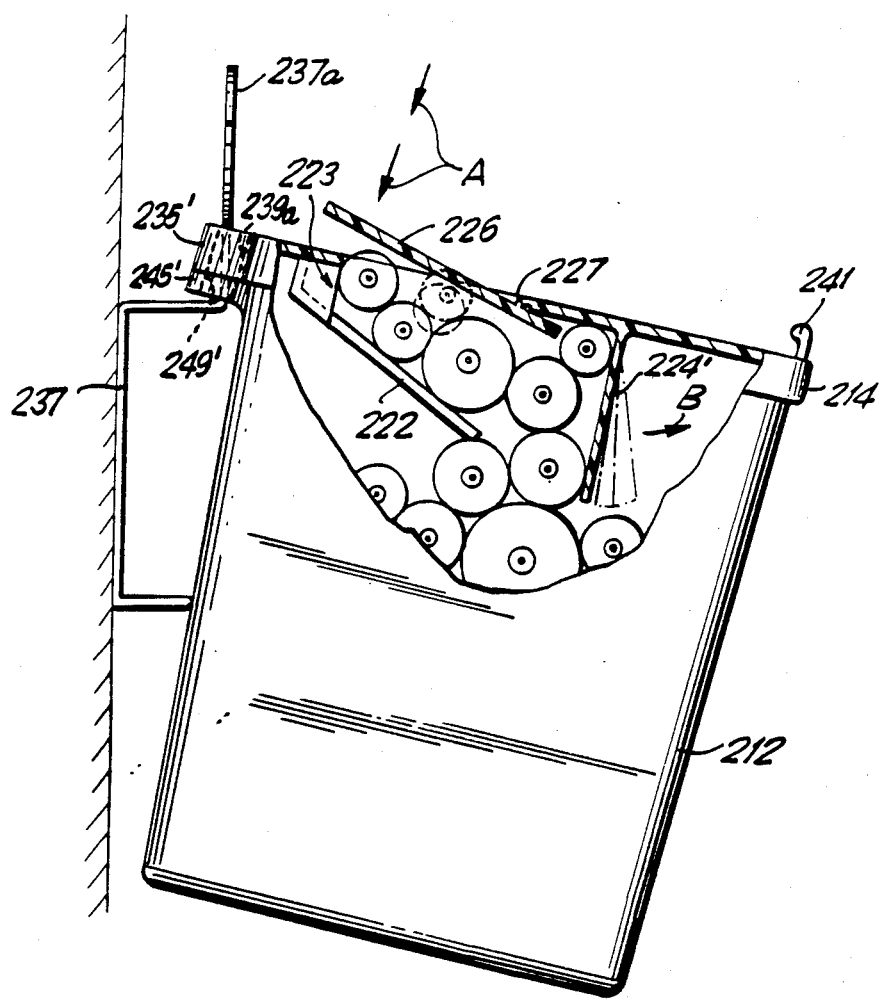
FIG. 14 is a view similar to FIG. 12 illustrating a preferred embodiment of back-drop/stop according to the present invention.

Turning now to FIG. 14, there illustrated a further aspect of the invention. According to this feature, the back-drop/stop member (indicated at 224') is adapted to be somewhat flexible. By providing such flexibility, it will be understood that secure closure of the receptacle can be achieved even if the receptacle is overfilled to such a point that discarded implements protrude beyond the top surface of top member 214. Accordingly, as closure panel 226 is rotated into its final closure position, it will urge any discarded implements in the overfill chamber (indicated generally at 223 and made up of the space bounded by the guide member, the back-drop/stop member and the top wall of the top member) back into the containment chamber, as illustrated by arrows A in FIG. 14. Because back-drop/stop 224' has flexibility, it will move forward to accommodate the implements in the overfill chamber, as indicated by arrow B in FIG. 14.

Thus, even if the receptacle reaches a dangerously overfilled condition, the receptacle can still be safely closed and secured for ultimate disposal. It will also be understood that even though there may be a small unfilled volume in the containment member because of the presence of the guide and back-drop/stop members, the minimal amount of lost storage space is far outweighed by the advantages achieved by the invention, particularly the deterence against hand entry, the side-by-side stacking of implements and the ability to securely and safely close the receptacle even when dangerously overfilled without contacting any of the implements in the overfill chamber.

In one embodiment of flexible back-drop/stop, the actual back-drop/stop member may be formed in a generally tapered configuration. Thus, it becomes thinner and more flexible towards its inwardly projecting distal edge. In another embodiment, the back-drop/stop member may be of substantially uniform thickness, but is secured to the top member through a weakened line of attachment, to form a hinge-like attachment.

Figure 15A:
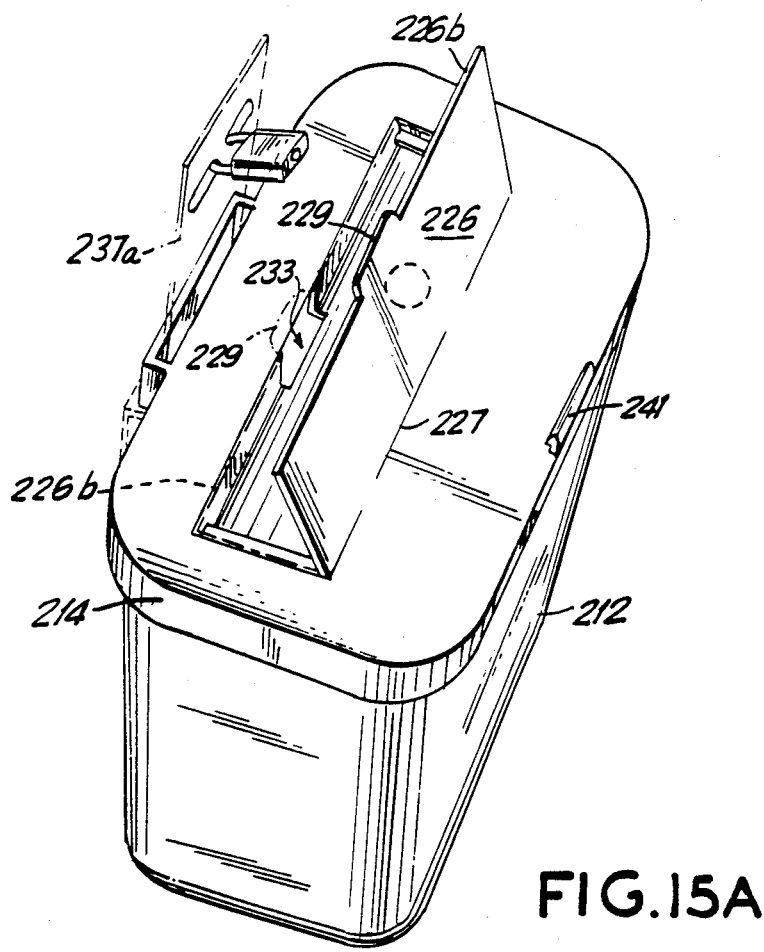
FIGS. 15A and 15B illustrate, respectively, a preferred closure means and method of closure for the closure member of the receptacle according to the present invention.
Figure 15B:
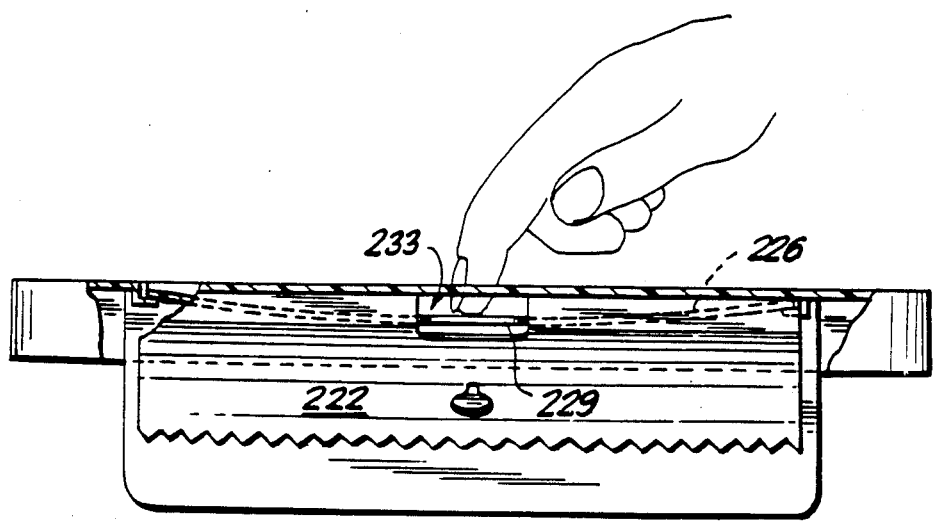

Turning now to FIGS. 15A and 15B, there is shown an alternate preferred embodiment of closure securing means according to the present invention which can be used instead of forming tabs 231 on the bottom of closure panel of 226. As here embodied, closure panel 226 includes locking tab-like projection 229 extending from its distal edge 226b. An opening, indicated at 233, is formed in the opposite portion of guide member 222. The opening 233 is positioned so as to be in correspondence with locking tab 229 on the closure member 226 which, in turn, also corresponds to the holding lug 241 to retain the top member in an open configuration.

In operation, a user releases closure panel 229 from retaining lug 241, then begins to close it substantially as described above. As the panel reaches its fully closed position, the user can simply push down in the area designated 237, causing panel 226 to bend slightly or assume a bowed configuration, to allow the locking tab 229 to snap into opening 233. Once tab 229 is received in opening 233, the receptacle is permanently secured for ultimate disposal.

It will be appreciated by those skilled in the art that the present invention in its broader aspects is not limited to the particular embodiments shown and described herein, and that variations may be made which are within the scope of the accompanying claims without departing from the principle of the invention and without sacrificing its chief advantages.

What is claimed is:

1. A self-contained receptacle for safely storing potentially dangerous implements such as hypodermic needles, scalpel blades and the like, comprising:
   a containment member proportioned to retain a plurality of implements; and
   a top member adapted to be attached to said containment member,
   said top member including an opening proportioned to receive a desired size of implements, a guide member extending generally angularly downwardly into said receptacle from said top member generally along one edge of said opening and a back-drop/stop member extending downwardly from said top member adjacent the side of said opening opposite the side adjacent to which said guide member is mounted, said back-drop/stop and guide members having distal edges which form a slot-like gap for allowing implements to drop into said receptacle, said back-drop/stop member and said guide member being positioned and proportioned relative to each other to cause at least a momentary slowing of travel of implements along said guide member to ensure that each implement assumes a generally horizontal orientation before actually dropping into said containment member such that implements inserted through said opening are aligned in a generally horizontal orientation by cooperation between said guide and back-drop/-stop members at said slot-like gap, thereafter to drop into said containment member for side-by-side stacking with other implements deposited therein.

2. A receptacle according to claim 1, wherein the distal edge of said guide member and an opposite edge of said opening are sharply jagged to deter hand entry into the receptacle.

3. A receptacle according to claim 1, wherein said top member is adapted to be sealed by a closure member once filled with implements to a desired level.

4. A receptacle according to claim 3, wherein said closure member is adapted to be snap-fit adjacent the opening in said top member.

5. A receptacle according to claim 4 which further includes a recessed shoulder formed around at least part of said opening for supporting said closure member when snap-fit adjacent said opening to allow the top surface of said closure member to be essentially flush with the top surface of said top member.

6. A receptacle according to claim 5 wherein said top member includes at least one guard tab formed at one edge of said opening and projecting over said opening to help deter hand entry into the receptacle, each said guard member being sufficiently spaced from a portion of said recessed shoulder to permit an edge of said closure member to become seated between said guard tab and said shoulder portion.

7. A receptacle according to claim 6, wherein the distal edge of each said guard tab is formed sharp to deter hand entry into the receptacle.

8. A receptacle according to claim 7, wherein the distal edge of said guide member and an opposite edge of said opening are sharply jagged to deter hand entry into the receptacle.

9. A receptacle according to claim 6, which further includes means for retaining said closure panel in place on top of said top member while said opening is to remain free to accept implements.

10. A receptacle according to claim 3, wherein said closure member is a panel-like member pivotally mounted to said top member such that it can be rotated from a first position with the opening free to accept implements to a second position wherein the closure member secures the opening to prevent access through the opening.

11. A receptacle according to claim 10, wherein said closure member includes hinge pin means receivable in recess means formed at the top of said top member.

12. A receptacle according to claim 11, wherein said closure panel includes locking tabs on its bottom to lockably engage edge portion of said opening when said closure member is positioned to secure the opening.

13. A receptacle according to claim 12, wherein said closure member further includes at least one additional closure locking tab formed generally near its pivotally connected edge, each said additional locking tab adapted to prevent the closure member from being pried open at its pivotally connected edge when said closure member is in the second position.

14. A receptacle according to claim 13, wherein the distal edge of said guide member and an opposite edge of said opening are sharply jagged to deter hand entry into the receptacle.

15. A receptacle according to claim 14, wherein each said additional locking tab is a generally L-shaped member having one leg recessed back from the pivotally connected edge of said closure member and its other leg proportioned to reside under said opposite edge of said opening when said closure member is in said second position.

16. A receptacle according to claim 10, wherein said closure member is integrally formed with said top member by pivotable mounting.

17. A receptacle according to claim 16, wherein said closure member is integrally mounted to said top member by a reduced thickness web member which forms a living hinge therebetween.

18. A receptacle according to claim 17, wherein said closure member includes an inward segment beyond said living hinge web extending into said opening, said inward segment having a jagged distal edge such that when said closure member is in said first position said jagged distal edge projects into said opening to deter hand entry into said receptacle, yet when said closure member is turned to the second position said jagged distal edge remains harmlessly within said receptacle while closure member seals said opening.

19. A receptacle according to claim 18, wherein said guide member is formed with a jagged distal edge to further deter hand entry into the receptacle.

20. A receptacle according to claim 19, wherein when said panel member is fabricated, said closure member extends generally perpendicular to the top surface of said top member and said living hinge/web extends from one edge of said opening to a surface portion of said closure panel to permit fabrication by two-part injection molding techniques.

21. A receptacle according to claim 3, wherein said top member includes a substantially continuous downwardly depending side wall member to form a protective skirt which overlaps said containment member to prevent access into said receptacle between said top and containment members.

22. A receptacle according to claim 10, wherein said top member includes a substantially continuous downwardly depending side wall member to form a protective skirt which overlaps said containment member to prevent access into said receptacle between said top and containment members.

23. A receptacle according to claim 16, wherein said top member includes a substantially continuous downwardly depending side wall member to form a protective skirt which overlaps said containment member to prevent access into said receptacle between said top and containment members.

24. A receptacle according to claim 3, wherein at least one of said top and containment members includes a flange adapted to be mounted to a support bracket for attachment to a wall or other support member.

25. A receptacle according to claim 24, wherein a said flange is formed on both said top and containment members.

26. A receptacle according to claim 10, wherein at least one of said top and containment members includes a flange adapted to be mounted to a support bracket for attachment to a wall or other support member.

27. A receptacle according to claim 26, wherein a said flange is formed on both said top and containment members.

28. A receptacle according to claim 16, wherein at least one of said top and containment members includes a flange adapted to be mounted to a support bracket for attachment to a wall or other support member.

29. A receptacle according to claim 27, wherein a said flange is formed on both said top and containment members.

30. A receptacle according to claim 11, wherein said closure member includes a tab-like locking tab projecting from its outward distal edge, and wherein said guide member includes a receiving opening positioned and proportioned to receive said locking tab such that said closure member can be urged towards its fully closed configuration so as to bend and allow said locking tab to snap into said receiving opening for permanently secure closure of said receptacle.

31. A receptacle according to claim 18, wherein said closure member includes a tab-like locking tab projecting from its outward distal edge, and wherein said guide member includes a receiving opening positioned and proportioned to receive said locking tab such that said closure member can be urged towards its fully closed configuration so as to bend and allow said locking tab to snap into said receiving opening for permanently secure closure of said receptacle.

32. A receptacle according to claim 24, wherein each said flange is formed along an edge closest to said one edge of said opening and is proportioned such that when mounted to a bracket on a wall, said guide member projects away from the wall, thereby to substantially prevent visual observation of the contents in the containment chamber and to provide a substantially tortuous path to deter hand entry into the containment chamber when installed on a wall bracket.

33. A receptacle according to claim 26, wherein each said flange is formed along an edge closest to said one edge of said opening and is proportioned such that when mounted to a bracket on a wall, said guide member projects away from the wall, thereby to substantially prevent visual observation of the contents in the containment chamber and to provide a substantially tortuous path to deter hand entry into the containment chamber when installed on a wall bracket.

34. A receptacle according to claim 28, wherein each said flange is formed along an edge closest to said one edge of said opening and is proportioned such that when mounted to a bracket on a wall, said guide member projects away from the wall, thereby to substantially prevent visual observation of the contents in the containment chamber and to provide a substantially tortuous path to deter hand entry into the containment chamber when installed on a wall bracket.

35. A receptacle according to claim 1, wherein said back-drop/stop member is adapted to be generally flexible such that when said closure member is closed, said flexible back-drop/stop member yields to allow any implements protruding from said opening to be forced into the receptacle merely by urging the closure member against them without requiring a person to contact of such implements.

36. A receptacle according to claim 35, wherein said back-drop/stop member is gradually tapered so as to be increasingly more flexible towards its distal end.

37. A receptacle according to claim 35, wherein said back-drop/stop includes a weakened line of connection between its distal end and said top member.

38. A receptacle according to claim 1, wherein the distal edge of said back-drop/stop member extends at least slightly deeper into said containment member than the distal edge of said guide member.

39. A receptacle according to claim 2, wherein the distal edge of said back-drop/stop member extends at least slightly deeper into said containment member than the distal edge of said guide member.

40. A receptacle according to claim 35, wherein the distal edge of said back-drop/stop member extends at least slightly deeper into said containment member than the distal edge of said guide member.

* * * * *